(12) United States Patent
Laine et al.

(10) Patent No.: US 8,916,122 B2
(45) Date of Patent: Dec. 23, 2014

(54) METHOD OF PRODUCING ALKOXYSILANES AND PRECIPITATED SILICAS FROM BIOGENIC SILICAS

(71) Applicant: Mayaterials, Inc., Ann Arbor, MI (US)

(72) Inventors: Richard M. Laine, Ann Arbor, MI (US);
Julien C. Marchal, Ann Arbor, MI (US);
Vera Popova, Ann Arbor, MI (US);
David J. Krug, Ann Arbor, MI (US)

(73) Assignee: Mayaterials, Inc., Ann Arbor, MI (US)

( * ) Notice: Subject to any disclaimer, the term of this patent is extended or adjusted under 35 U.S.C. 154(b) by 119 days.

(21) Appl. No.: 13/737,103

(22) Filed: Jan. 9, 2013

(65) Prior Publication Data

US 2013/0184483 A1 Jul. 18, 2013

Related U.S. Application Data

(60) Provisional application No. 61/587,188, filed on Jan. 17, 2012.

(51) Int. Cl.
*C01B 33/039* (2006.01)

(52) U.S. Cl.
CPC ..................................... *G07F 7/07* (2013.01)
USPC ........... 423/335; 423/324; 423/339; 423/345; 556/464

(58) Field of Classification Search
USPC ................... 556/464; 423/324, 335, 345, 339
See application file for complete search history.

(56) References Cited

U.S. PATENT DOCUMENTS

| | | | | |
|---|---|---|---|---|
| 5,099,052 A | * | 3/1992 | Laine et al. ................... | 556/443 |
| 2011/0206592 A1 | | 8/2011 | Laine et al. | |

OTHER PUBLICATIONS

Chaudry, D.S.; Jollands, M.C. "Characterization of Rich Hull Ash", J. Appl. Poly. Sci. 2004, 93, pp. 1-8.
Freitas, J. C. C.; Emmerich, F. G.; Bonagamba, T. J.; "High-Resolution Solid-State NMR Study of the Occurrence and Thermal Transformations of Silicon-Containing Species in Biomass Materials", Chem. Mater.; 2000; 12 pp. 711-718.
Teng, H.; Lin, H.-C.; Ho, J.-A.; "Thermogravimetric Analysis on Global Mass Loss Kinetics of Rice Hull Pyrolysis", Ind. Eng. Chem. Res.; 1997 36, pp. 3974-3977.
Sun, L.; Gong, K.; "Silicon-Based Materials from Rice Husks and Their Applications", Ind. Eng. Chem. Res.; (Review); 2001; 40(25); pp. 5861-5877.
T. Coradin, P. J. Lopez, "Biogenic Silica Patterning: Simple Chemistry or Subtle Biology?", Chem. BioChem. 4 (2003), pp. 251-259.
D. J. Benke, M. S. Wainwright, K.D.P. Nigam, T.R. Rao, "Kinetics of Silica Dissolution from Rice Husk Char", The Canadian Journal of Chemical Engineering, The Berkeley Electronic Press, 2006—Non catalytic.
J. A. Amick, "Purification of Rice Hulls as a Source of Solar Grade Silicon for Solar Cells", J. Electrochem. Soc.: Solid-State Sci. Tech. 129, pp. 864-866 (1982).
L. P. Hunt, J. P. Dismukes, J. A. Amick, A. Schei, K. Larsen, "Rice Hulls as a Raw Material for Producing Silicon", J. Electrochem. Soc.: Solid-State Sci. Tech. 131 pp. 1683-1686 (1984).
M.Z. Asuncion, I. Hasegawa, J. Kampf, R.M. Laine, "The selective dissolution of rice hull ash to form [OSiO1.5]8[R4N] 8 (R=Me, CH2CH2OH) octasilicates. Basic nanobuilding blocks and possible models of intermediates formed during biosilification processes", Materials Chemistry 15, pp. 2114-2121 (2005).
H. Cheng, R. Tamaki, R.M. Laine, F. Babonneau, Y. Chujo, and D.R. Treadwell, "Neutral Alkoxysilanes from Silica", J. Am. Chem. Soc. 122, pp. 10063-10072 (2000).
C. L. Frye, "Stable Silicon Heterocyclic Derivatives of Branched Alkanediols", J. Org. Chem. vol. 34, No. 9, 1969, pp. 2496-2499.

\* cited by examiner

*Primary Examiner* — Sudhakar Katakam
*Assistant Examiner* — Pancham Bakshi
(74) *Attorney, Agent, or Firm* — Kubotera & Associates, LLC

(57) ABSTRACT

A method of producing alkoxysilanes and precipitated silicas from biogenic silicas is provided. In a first step, biogenically concentrated silica is mixed with a liquid polyol to obtain a mixture, and then the mixture is heated. In a second step, a base is added to obtain a reaction mixture. In a third step, the reaction mixture is filtered to remove the carbon enriched RHA or other undissolved biogenic silica and recover the solution of alkoxysilane and alcoholate. In a fourth step, alkoxysilane is purified by filtering, distilling, precipitating or extracting from the original reaction solution to precipitate various forms of silica. In a final step, residual base present in alkoxysilane is neutralized to eliminate the residual alkali metal base.

10 Claims, 14 Drawing Sheets

| Compound | Boiling Point °C (mm Hg) | Recrystallized from |
|---|---|---|
| I | | Hexane |
| II | 130-133 (0.8) | |
| III | | Hexane |
| IV | 134-137 (0.5) | |
| V | 150-155 (0.8) | |
| VI | | MeOH |
| VII | 110 (4.5) | |
| VIII R = Bu | 88-90 (0.15) | |
| VIII R = Me | 67 (2.4) | |
| IX | 119 (0.65) | |

Reaction (4)

Reaction (6)

| Time (h) | Dissolution (%) | Moles of silica in solution |
|---|---|---|
| 5 | 15.4 | 0.15 |
| 11 | 20.2 | 0.20 |
| 17 | 23.4 | 0.23 |
| 23 | 26.7 | 0.26 |

TABLE 1

FIG. 22

METHOD OF PRODUCING ALKOXYSILANES AND PRECIPITATED SILICAS FROM BIOGENIC SILICAS

CROSS-REFERENCE TO RELATED APPLICATIONS

The application claims the benefit under 35 U.S.C. 119(e) of the provisional application No. 61/587,188, filed on Jan. 17, 2012.

BACKGROUND OF THE INVENTION

The present invention relates to a method of producing alkoxysilanes and precipitated silicas from biogenic silicas. Many plants ranging from diatoms to grasses to trees take soluble silica from water sources and transport it within their systems and deposit it in various forms and places ranging from the shells of diatoms, to the cells of hard woods, to rice hulls and stalks. In the majority of instances the transport systems involved in the biosilification process are not designed to also transport heavy metals. Consequently biogenically deposited silica is relatively free of heavy metal impurities making it a prospective source for high purity silicon containing materials ranging from alkoxysilanes to silica to silicon nitride to silicon carbide to silicon metal. Biogenically produced silica can be defined as being a sustainable resource as for example in the case of any currently grown silica accumulating plant. Their availability in industrially meaningful quantities as byproducts of existing human efforts to produce food and fiber makes this resource commercially important.

For example, according to Non-Patent references 1 to 4, rice hulls are produced in 100 million ton quantities annually as a generally undesirable byproduct of rice milling. They can contain 12-20 wt % silica in an amorphous, high surface area form. There are now multiple studies in the patent and open literature on the recovery of silicon containing materials from rich hulls. Thus, rice hulls and rice hull ash have been used as a starting point to make solar grade silicon, silicon carbide, silicon nitride and also to recover relatively pure silica through dissolution with a base such as alkali or alkaline earth carbonates or hydroxides, tetramethylammonium or choline hydroxide as noted in the following references and references used in these papers which are incorporated herein as prior art.

LIST OF NON-PATENT REFERENCES

1. Chaudry, D. S.; Jollands, M. C. "Characterization of Rich Hull Ash", J. Appl. Poly. Sci. 2004, 93, 1-8.
2. Freitas, J. C. C.; Emmerich, F. G.; Bonagamba, T. J.; "High-Resolution Solid-State NMR Study of the Occurrence and Thermal Transformations of Silicon-Containing Species in Biomass Materials", Chem. Mater.; 2000; 12 711-718
3. Teng, H.; Lin, H.-C.; Ho, J.-A.; "Thermogravimetric Analysis on Global Mass Loss Kinetics of Rice Hull Pyrolysis", Ind. Eng. Chem. Res.; 1997 36 3974-3977.
4. Sun, L.; Gong, K.; "Silicon-Based Materials from Rice Husks and Their Applications", Ind. Eng. Chem. Res.; (Review); 2001; 40(25); 5861-5877.
5. T. Coradin, P. J. Lopez, "Biogenic Silica Patterning: Simple Chemistry or Subtle Biology?", Chem. BioChem. 4 (2003), 251-259.
6. L. Sun, K. Gong, "Silicon-Based Materials from Rice Husks and Their Applications", Ind. Eng. Chem. Res. 40, 5861-5877 (2001).
7. D. J. Benke, M. S. Wainwright, K. D. P. Nigam, T. R. Rao, "Kinetics of Silica Dissolution from Rice-husk Char", The Canadian Journal of Chemical Engineering, The Berkeley Electronic Press, 2006—Non catalytic.
8. J. A. Amick, "Purification of Rice Hulls as a Source of Solar Grade Silicon for Solar Cells", J. Electrochem. Soc.: Solid-State Sci. Tech. 129, 864-6 (1982).
9. L. P. Hunt, J. P. Dismukes, J. A. Amick, A. Schei, K. Larsen, "Rice Hulls as a Raw Material for Producing Silicon", J. Electrochem. Soc.: Solid-State Sci. Tech. 131 1683-6 (1984).
10. M. Z. Asuncion, I. Hasegawa, J. Kampf, R. M. Laine, "The selective dissolution of rice hull ash to form $[OSiO_{1.5}]_8[R_4N]_8$ (R=Me, $CH_2CH_2OH$) octasilicates. Basic nanobuilding blocks and possible models of intermediates formed during biosilification processes", Materials Chemistry 15, 2114-21 (2005).
11. H. Cheng, R. Tamaki, R. M. Laine, F. Babonneau, Y. Chujo, and D. R. Treadwell, "Neutral Alkoxysilanes from Silica", J. Am. Chem. Soc. 122, 10063-72 (2000).
12. M. Z. Asuncion, I. Hasegawa, J. Kampf, R. M. Laine, "The selective dissolution of rice hull ash to form $[OSiO_{1.5}]_8[R_4N]_8$ (R=Me, $CH_2CH_2OH$) octasilicates. Basic nanobuilding blocks and possible models of intermediates formed during biosilification processes", Materials Chemistry 15, 2114-21 (2005).
13. C. L. Frye, "Stable Silicon Heterocyclic Derivatives of Branched Alkanediols", J. Org. Chem. 1969, vol. 34, No. 9, 2496-2499.

LIST OF PATENT REFERENCE

U.S. Patent Publication 2011/0206592

In all of these cases, the silica content in the rice hulls (approximately 12-20 wt %) or rice hull ash (RHA, approximately 80-95 wt %) is used as a reactant in further processing of the target products. In the instances where silica is dissolved with strong base, the base is used as a stoichiometric reactant such that for every $SiO_2$ dissolved, two base molecules e.g. MOH or $M_2CO_3$ are used where M is an alkali metal but could be an alkaline earth metal, M'(OH)$_2$ or M'O or M'CO$_3$.

The general dissolution process is that seen in Reaction (1). There are numerous studies on the kinetics of this process as discussed by Benke et al. It is important to note that at industrial scales this reaction is often carried out in a furnace at temperatures exceeding 1300° C. with a subsequent cost for the capital equipment needed and the energy expended.

$$2MOH + SiO_2 \xrightarrow{H_2O} M_2SiO_3 \qquad (1)$$

If one wants to recover silica from $M_2SiO_3$ for example to form high surface area, precipitated or colloidal silica; it is necessary to add stoichiometric quantities of acid to a solution of $M_2SiO_3$ typically in water as suggested by Reaction (2) where sulfuric acid is used as an exemplary acid. Note that there are costs associated with disposal of $M_2SO_4$ and byproduct water also produced.

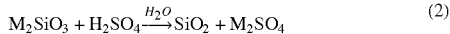

$$M_2SiO_3 + H_2SO_4 \xrightarrow{H_2O} SiO_2 + M_2SO_4 \quad (2)$$

If it were possible to dissolve silica using only catalytic quantities of base, then it would be possible to greatly reduce the cost of recovering and using biogenically derived silica for many of the purposes discussed above. Furthermore, this would imply that the acid needed to recover the dissolved silica would only be the quantities needed to neutralize the catalytic base, reducing process costs, reducing the possible consequences of unintended spills, potential for pollution and the cost of recycling spent acid and acid byproducts.

Another important function of such a process would be to inexpensively and accurately reduce the total silica content in rice hull ash with the intent to precisely raise the relative carbon content. This important, separate function would permit the selection of C:$SiO_2$ stoichiometries in the recovered, extracted RHA that are more amenable to transformation into SiC, $Si_3N_4$ and more importantly Si metal. Further, such a process would provide a different platform from which to perform silicon purification as the volumes of material to be subjected to purification would be greatly reduced, hence the process will be more economical.

A related process using fumed silica produced via Reaction (3) has been described by several of the inventors in: R. M. Laine, D. J. Krug, J. C. Marchal, A. S. McColm "Low cost routes to high purity silicon and derivatives thereof, U.S. 2011/0206592 Pub. Aug. 25, 2011 and is hereby incorporated as prior art.

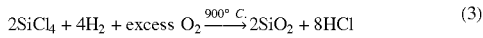

$$2SiCl_4 + 4H_2 + \text{excess } O_2 \xrightarrow{900° C.} 2SiO_2 + 8HCl \quad (3)$$

SUMMARY OF THE INVENTION

According to an aspect of the present invention, a method of producing alkoxysilanes and precipitated silicas from biogenic silicas is provided. In a first step, freshly produced or aged biogenically concentrated silica in a milled or un-milled form that has received prior treatment that may arise from a first acid purification step or simply a first heating in water to dissolve basic components achieving pH values of 9 or greater is mixed with a liquid polyol such as ethylene glycol, 1,2; 1,3; 2,3 or 1,4-diols or triols such as glycerol or triethanolamine or trishydroxy-methylamine, mixtures thereof or analogous compounds obvious to one practiced in the art.

In a second step, sufficient base such as LiOH, NaOH, KOH, CsOH, RbOH or mixtures thereof in catalytic amounts ranging from 0.25-50 mol % but preferably 1-20 mol % and most preferably 3-15 mol % can be added either as a solid or preferably predissolved in the solvent of choice such that the resulting dispersion containing sufficient solvent/reactant so that the mixture is easily stirred is then heated to a temperature where water, the by-product of the dissolution process will distill out.

In a specific modification, in addition to the diol, triol or mixtures thereof, a second lower boiling liquid that can azeotrope water can be added to remove water at a lower temperature to also drive silica dissolution and formation of Si—O—C linkages while minimizing loss of the diol from the reaction solution.

The reaction temperature may be aided by changes in pressure to effect faster reaction rates.

In a third step defined by the amount of silica that has been solublized in the form of an alcoholate and alkoxysilane; the reaction mixture is then filtered to remove the carbon enriched RHA or other undissolved biogenic silica and recover the solution of alkoxysilane and the alcoholate substantially free of solids. The solution may be cooled to precipitate the alcoholate, which can be filtered off and reused as base in a second or third or fourth etc dissolution reaction. The recovered carbon enriched RHA may be used for processing other products including SiC, $Si_3N_4$, or simply high purity silicon.

In a fourth step, the thus purified alkoxysilane will contain four Si—O—C bonds in the form of a polyalkoxysilane or more preferably as a tetraalkoxysilane or spirosiloxane that can be further purified by filtering, distilling, precipitating or extracting from the original reaction solution and can be used as is for forming other types of silicon containing chemicals or may be treated with water or acid to precipitate various forms of silica.

In a final step, any residual base present in the recovered alkoxysilane can be neutralized in a variety of ways to eliminate the residual alkali metal base present in the form of a salt that can be removed by filtration or precipitation leaving a pure alkoxysilane free of metal impurities; alternately these impurities can be removed using ion exchange materials.

In this invention, we demonstrate that it is possible to catalytically dissolve the silica in RHA using a novel method that employs a catalytic amount of base and a high boiling solvent wherein said solvent contains at least two hydroxyl groups capable of chelating the silicon atom as it is catalytically extracted from any silica surface. A representative general reaction that uses ethylene glycol or $EGH_2$ is as follows. In this process the cation serves to stabilize intermediate anions that form on the silica surface. Because the proposed intermediate $Si(EG)_2$ is a spirosiloxane, it is not anticipated to be stable under the reaction conditions but rather the ring opened species $Si(OCH_2CH_2OH)_4$ appears to form in solution. As shown in FIG. 19, such a process was described in Non-Patent reference 11, the open literature by Laine et al (referred to Reaction (4) shown in FIG. 19), which is incorporated herein as prior art.

This original publication might be construed to be limiting in terms of the current invention; however, these studies were done using fumed silica, which derives from reaction of $SiCl_4$ in $H_2/O_2$ flames; with $SiCl_4$ coming from silicon metal itself (Reaction (3)). This type of silica is amorphous, high surface area and also contains small amounts of Si—Cl bonds. It is not at all clear that rice hull ash, which consists of intimate mixtures of significant amounts of hydrophobic carbon, inorganic minerals and partially crystalline silica will behave the same way. Indeed, one might anticipate that the hydrophobic RHA carbon, which in some instances can be as much as 55 wt % of the RHA might interfere with the wetting needed to effect the above extraction reaction.

Indeed, according to Non-Patent reference 12, that is, work by Asuncion et al (incorporated here as prior art) demonstrates that even with the use of stoichiometric quantities of $Me_4NOH$ or chlorine hydroxide, far stronger bases than alkali hydroxides, it is not possible even with heating to extract greater than 50 wt % of RHA silica, whereas in our invention we are able to use only catalytic amounts of the lower basicity alkali hydroxides. In these instances, the RHA was not milled.

Thus, it is not obvious to one of average skill that one can substitute RHA for fumed silica. A further important aspect of this invention is that it is not necessary to add base even in catalytic amounts to affect dissolution. This is because on combustion of rice hulls, residual alkali and alkaline earth oxides, hydroxides and carbonates are produced that are inherent impurities in the starting rice hull ash.

For example, RHA can contain 1-3 wt % $K_2O$ and 0.2-0.3% CaO and some $Na_2O$. Thus, it is actually not necessary to even add base to effect catalytic dissolution of silica as seen in Examples 1-4. In Example 2, after 25 h of dissolution time, some 15 wt % of the available silica has been dissolved. At 30 h of reaction 17 wt % of the silica is dissolved (FIGS. 4 and 5). There appears to be the beginning of a slowdown in reaction at this time. In an effort to improve the rate of reaction by first promoting dissolution of the basic components, Examples 3 and 4 demonstrate that addition of water followed by refluxing to the point where the solution pH rises above 9 followed by water removal and coincident addition of $EGH_2$ leads to an increase in the rate of dissolution compared with the results without water addition. However, dissolution asymptotes in these latter examples at about 17 wt % dissolved silica.

It is also advantageous to add additional but catalytic amounts of base simply to speed up the overall dissolution process as seen in Examples 5 and 6.

Example 5 (FIGS. 10 and 11) contrasts with Example 6 using un-milled RHA where it is obvious that milling creates fresh surface area that is important in the rate of silica dissolution with the data suggesting that un-milled material, without a water reflux, asymptotes at just 10 mol % dissolved silica. This is the same kind of asymptote seen by Asuncion et al but at much lower amounts of dissolved silica indicating the non-obviousness of our invention.

In Example 6, 3 mol % additional KOH is added to milled RHA in $EGH_2$ and the dissolved silica after 30 h is now 24 wt % (FIGS. 12 and 13).

A further result of this invention is that the dissolved silica is present in the form $Si(OCH_2CH_2OH)_4$ as demonstrated by the TGA ceramic yield somewhat greater than 22 wt %. It is important to note that further $EGH_2$ can be removed from $Si(OCH_2CH_2OH)_4$ to form a polymeric equivalent of $Si(EG)_2$ or $S(OCH_2CH_2O)_2$ which would be a spirosiloxane if it were not polymerized. However other diols offer the opportunity to generate base stable spirosiloxanes that are distillable as discussed below. Thus one can distill off additional $EGH_2$ to make viscous oligomers and/or polymers that can contain up to 40-44 wt % silica and that remain mostly water soluble. This then represents the types of products that can be produced during silica dissolution.

Example 7 uses 10 mol % KOH and enables one to dissolve 52 wt % silica in just 12 h, as seen in FIGS. 15 and 16. Thus, we can greatly increase the total amount of silica dissolved, well above the initial asymptote region and still with minor catalytic amounts of base.

As noted above, it is advantageous to first reflux the RHA in water to dissolve the basic components to achieve aqueous pH values greater than 9 prior to attempting to perform catalytic extraction. As seen in Example 8 a prior reflux in water coincident with milling leads to total dissolved silica contents at approximately 40 wt % at 30 h even with much larger quantities of RHA as seen in FIGS. 17 and 18. Example 8 also demonstrates that NaOH can be used in place of KOH to achieve similar dissolution rates. For one of average skill this implies that other group 1 metal hydroxides including Li, Cs and Rb would also work as catalysts for this same reaction.

Indeed from the prior art, it appears that the catalytic dissolution of fumed silica is linear with concentration; whereas this is not the case for RHA which appears at lower catalyst amounts to exhibit asymptotic behavior as found by Asuncion et al. Nonetheless the fact that 0-10 mol % added base relative to total RHA silica content of 100 mol % coupled with milling and refluxing with water is effective in dissolving reasonable to significant portions of RHA silica with the overall goals of:

(1) greatly reducing the base needed to dissolve any biogenic silica but especially RHA;
(2) Increasing the rate of dissolution by using milling and water reflux to produce solutions with pH greater than 9.
(3) recovering said silica in the form of an alkoxysilane, e.g. $Si(CH_2CH_2OH)_4$ which in turn can be hydrolyzed to produce silica or used as is, or converted to a distillable intermediate.
(4) adjusting the $SiO_2$:C ratio within the remaining extract RHA towards that needed for carbothermal reduction to SiC or
(5) adjusting the $SiO_2$:C ratio within the remaining extract RHA towards that needed for carbothermal reduction to very pure Si.

A further aspect of this invention is that other biological sources of silica can also be used as demonstrated in Examples 9 and 10 where bagasse derived silica and diatomaceous earth also work well.

As noted above, it is also possible to use other diols and triols rather than $EGH_2$ as demonstrated in Examples 11 and 12. As briefly noted above, stable spirosiloxanes have been produced using selected diols other than $EGH_2$ as discussed by Frye and as illustrated in reaction (5) which is not meant to be limiting. However, the Frye process uses $Si(OEt)_4$ as the starting point which is produced from $Si_{met}$ rather than any form of silica.

Frye finds that spirosiloxanes as shown schematically in Reaction (5) shown in FIG. 20 which are not meant to be limiting and can be quite stable, even in the presence of base and can be distilled or dissolved and recrystallized from organic solvents to high degrees of crystallinity as shown in FIG. 1. Thus, judicious choice of diols offers access to additional methods of purifying silica extracted from RHA or bagasse or diatomaceous earth. Thus, Non-Patent reference No. 13, the work of Frye is incorporated here as prior art.

Still another aspect of this invention is that it is possible to remove the water during the catalytic dissolution process by using a non-solvent that can form azeotrope with water allowing the reaction to be run at still lower temperatures as demonstrated in Example 11 where toluene azeotropes water at temperatures as low as 100° C. to drive dissolution with only minimal loss of the diols.

BRIEF DESCRIPTION OF THE DRAWINGS

FIG. 22 shows Table 1 showing percentage of total silica (0.972 moles total) dissolved in solution in Example 13, according to the embodiment of the present invention.

PREFERRED EMBODIMENT OF THE PRESENT INVENTION

All of these are aspects of the products resulting from the current invention.

Figure 21:
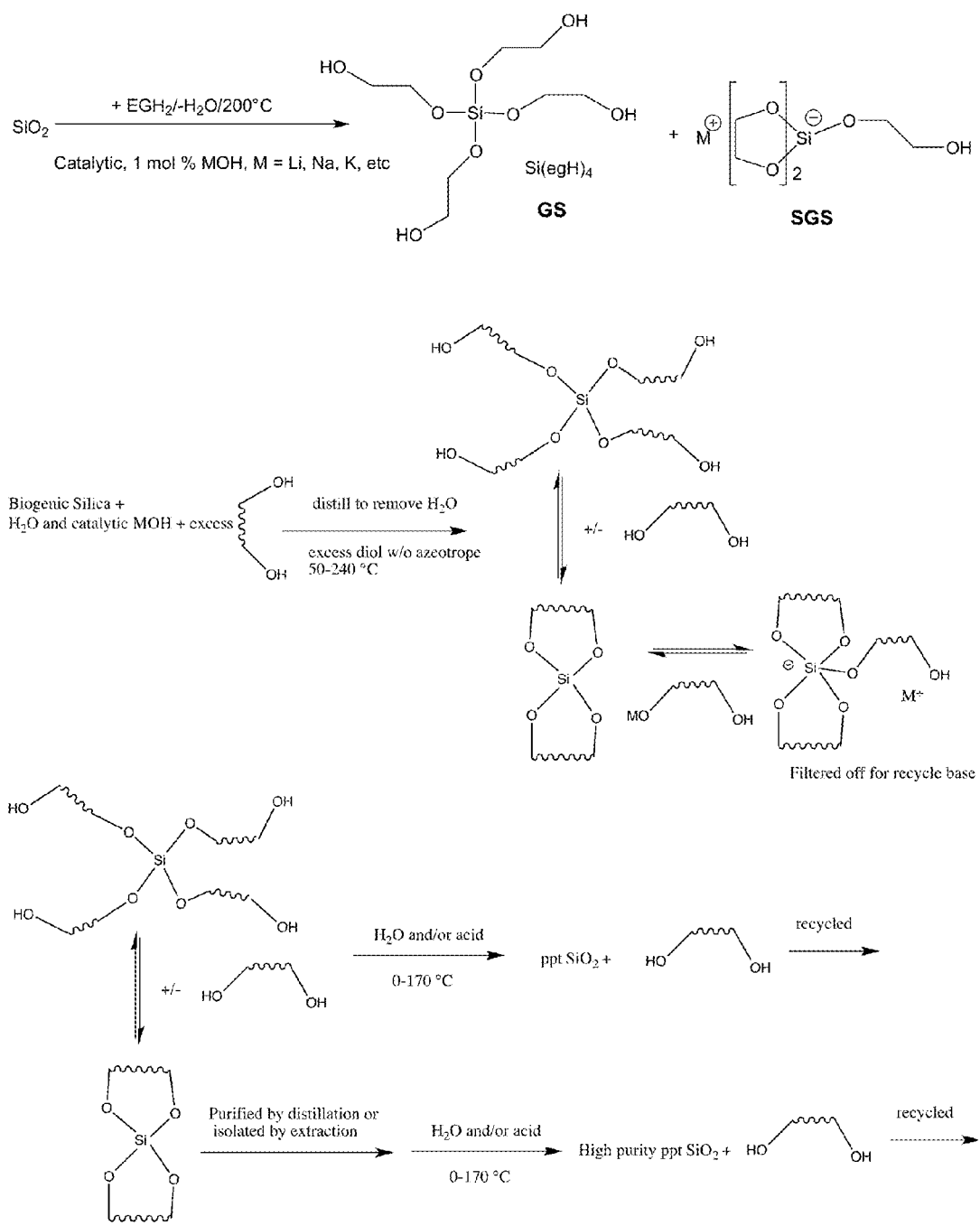
FIG. 21 shows the general process (Reaction (6)) which has been developed according to the embodiment of the present invention.

The general process developed here is presented in Reaction (6) shown in FIG. 21. On filtering and cooling the reaction solution, the sodium glycolato silicate or SGS precipitates from the resulting solution and can be recovered nearly quantitatively and recycled as demonstrated in Example 13. Thus, the amount of base used for silica dissolution is minimal indeed it is possible to just add the water distilled out of the original reaction to promote silica precipitation as demonstrated in Example 14. One can also use acids to promote precipitation as illustrated in Example 15 and in a coincidentally submitted patent. If other diols are used then compounds similar to SGS will form and are called hereafter alcoholates.

Example 1

Dissolution of Un-Milled RHA in $EGH_2$, No Water Reflux, No Catalyst (UM-NR-NC)

Figures 1, 2:
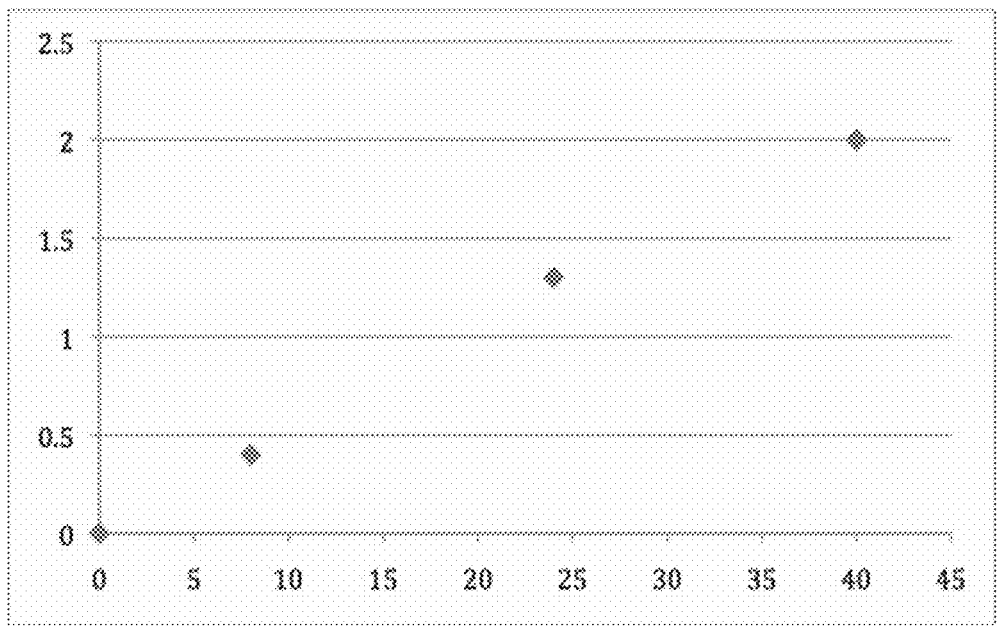
FIG. 1 shows B.p. or recrystallization solvent for compounds, according to Non-Patent reference No. 13.
FIG. 2 shows weight percent $SiO_2$ dissolved from un-milled RHA, no reflux, no catalyst, vs time (h) in Example 1 according to an embodiment of the present invention.
Figure 3:
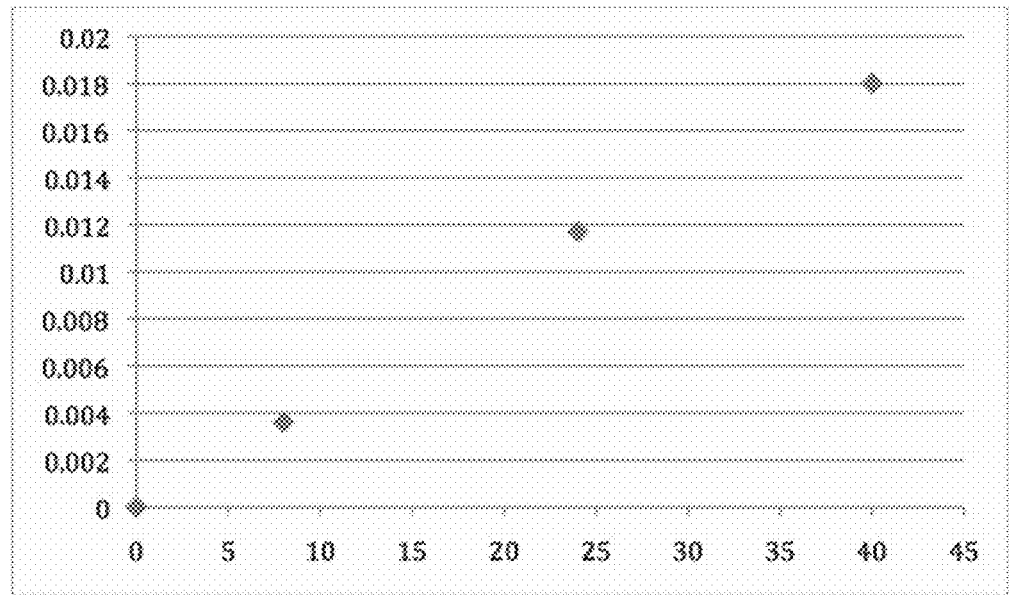
FIG. 3 shows moles of $SiO_2$ dissolved, from un-milled RHA, no reflux, no catalyst vs time (h) in Example 1 according to the embodiment of the present invention.

To a dry 2000 mL round-bottomed flask, was added 60 g of un-milled RHA (containing 0.9 moles of silica) and 1 L of $EGH_2$. The reaction was stirred and heated to 200° C. to distill out water forming with the dissolution of silica over a 40 h period. During this time, fresh $EGH_2$ was added regularly to compensate for the amount of $EGH_2$ distilled off. After 8/24/40 h, 5 mL aliquots were taken, filtered, weighed and then heated to conduct a loss on ignition test (LOI), to determine the amount of silica dissolved in solution. The results are shown in FIGS. 2 and 3.

Example 2

Dissolution of Milled RHA in $EGH_2$, No Water Reflux, No Catalyst

Figure 4:
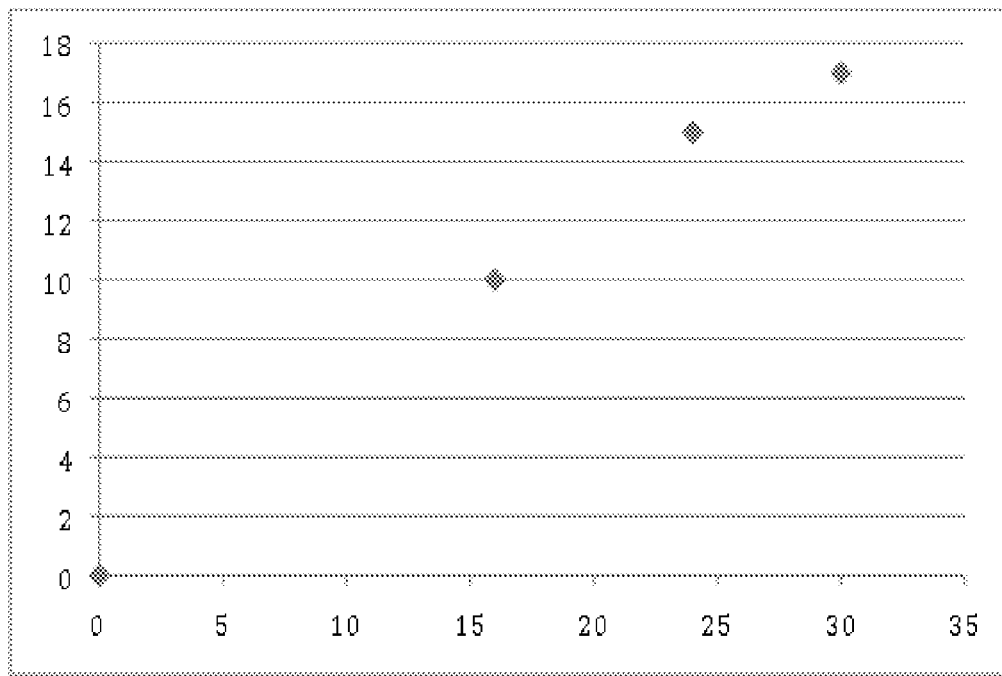
FIG. 4 shows weight percent silica dissolved, from milled RHA, without reflux, no catalyst, as a function of time (hours) in Example 2 according to the embodiment of the present invention.
Figure 5:
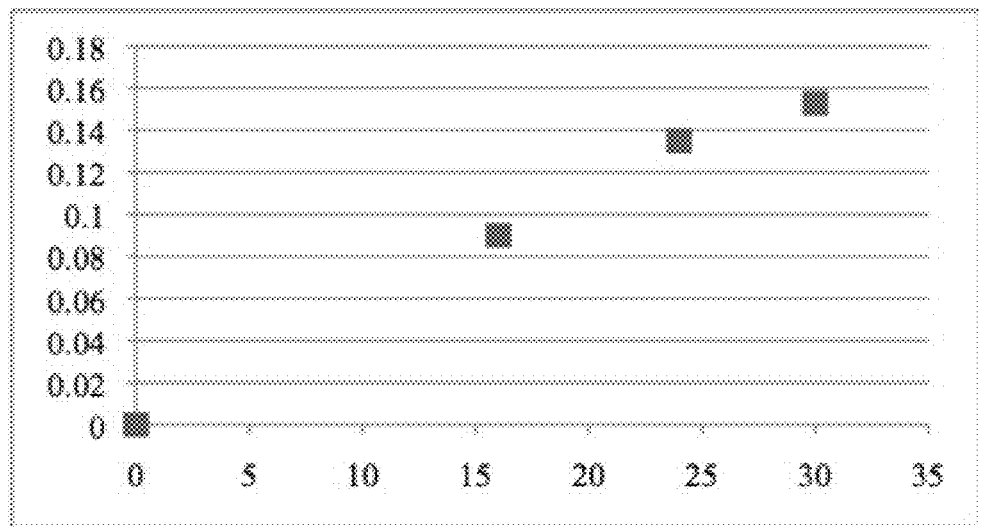
FIG. 5 shows moles of silica dissolved, from milled RHA, without reflux, no catalyst, as a function of time (hours) in Example 2 according to the embodiment of the present invention.

To a dry 2000 mL round-bottomed flask, equipped with a distillation condenser fitted with a collection flask and kept under $N_2$; was added 60 g of milled RHA (containing 0.9 moles of silica) and 1 L of EG. The reaction was stirred magnetically and heated to approximately 200° C. to distill out water forming with the dissolution of silica over a 40 h period. During this time, fresh $EGH_2$ was added regularly to compensate for the amount of $EGH_2$ distilled off. After 16/24/30 h, 5 mL aliquots were taken, filtered, weighed and then heated to conduct a loss on ignition test (LOI), to determine the amount of silica dissolved in solution. FIGS. 4 and 5 show results.

Example 3

Dissolution of Un-Milled RHA in $EGH_2$, with Water Reflux, No Catalyst

Figure 6:
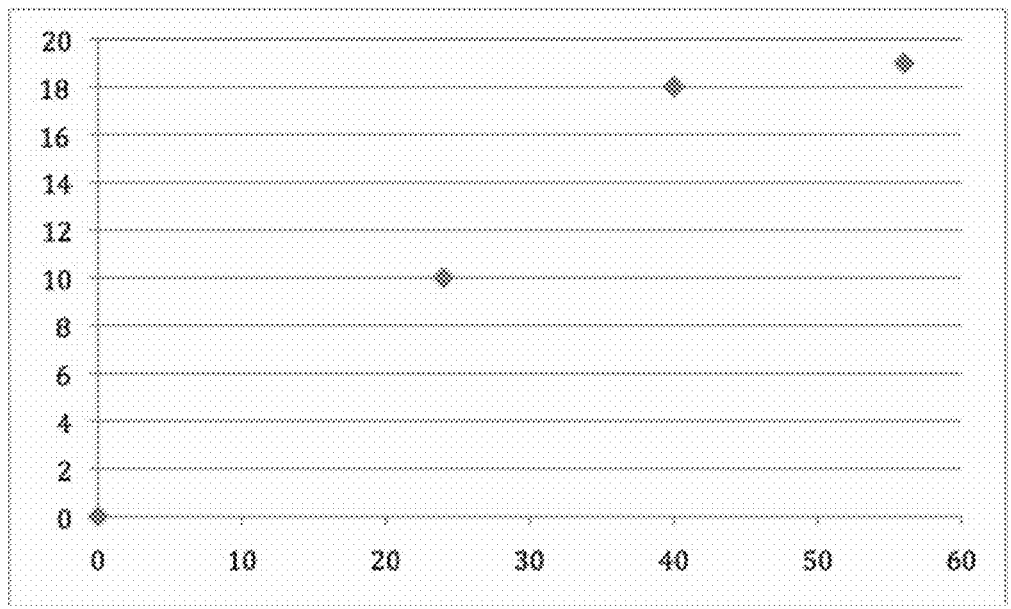
FIG. 6 shows weight percent silica dissolved, from un-milled RHA, with reflux, no catalyst, as a function of time (h) in Example 3 according to the embodiment of the present invention, note asymptote.
Figure 7:
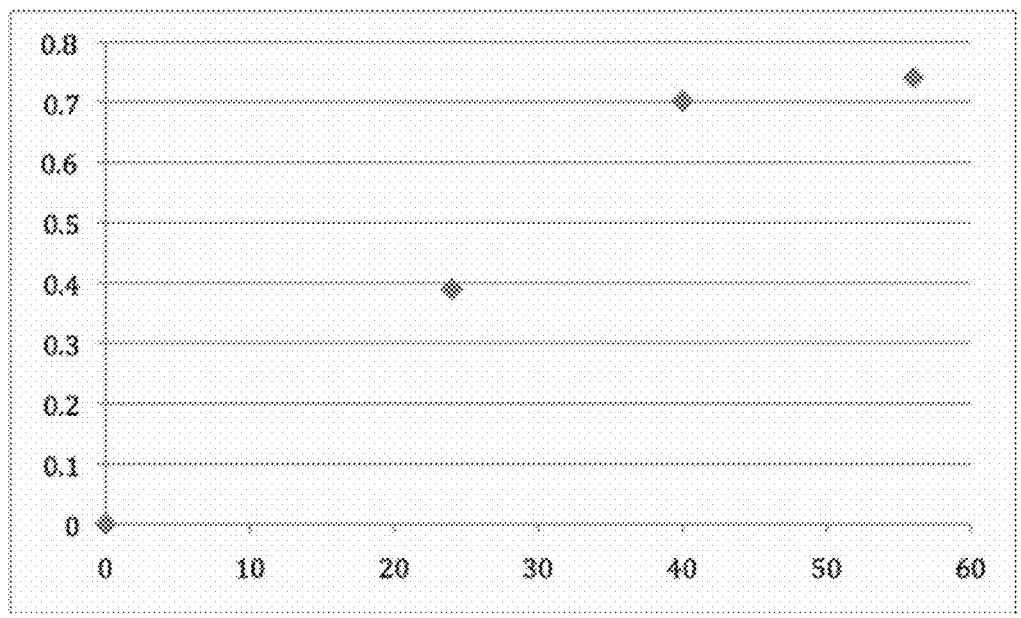
FIG. 7 shows moles $SiO_2$ dissolved from un-milled RHA, with reflux, no catalyst, vs time (hours) in Example 3 according to the embodiment of the present invention.

To a dry 3 L round-bottomed flask, equipped with a reflux condenser kept under $N_2$; was added 260 g of untreated RHA (containing 3.9 moles of silica), and 2 L of water. The reaction was stirred at 100° C. for 48 h. While keeping the reaction hot, the reflux condenser was switched to distillation mode. Water was distilled off and after every 500 mL of water distilled off; 500 mL of $EGH_2$ was added. At this point the temperature was increased to approximately 200° C. to effect efficient silica dissolution by removal of water formed coincident with some ethylene glycol. Fresh ethylene glycol was added regularly to compensate for the amount of ethylene glycol distilled off. After 24/40/56 h, 5 mL aliquots were taken, filtered, weighed and LOI was run to determine the amount of silica dissolved in the solution. FIGS. 6 and 7 record the results.

Example 4

Dissolution of Milled RHA in $EGH_2$, with Water Reflux, No Catalyst

Figure 8:
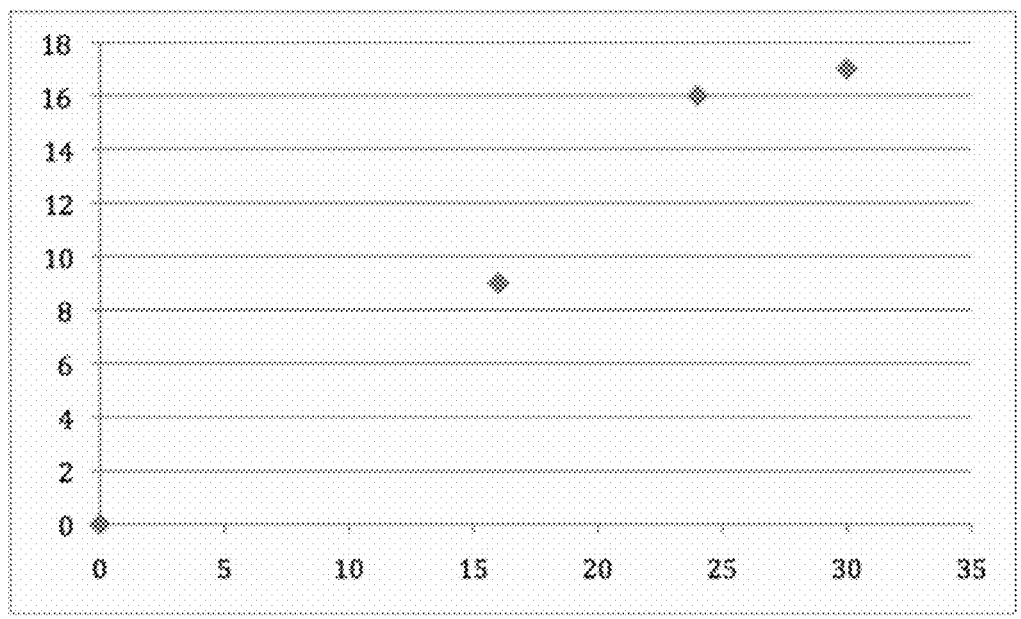
FIG. 8 shows percent silica dissolved from milled RHA, with reflux, no catalyst, as a function of time (hours) in Example 4 according to the embodiment of the present invention, note asymptote.
Figure 9:
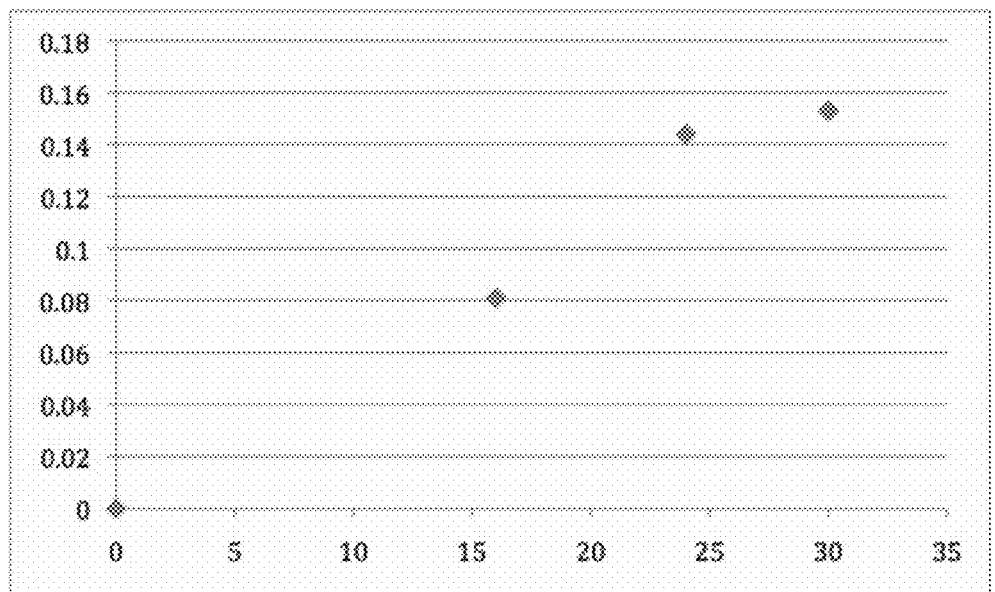
FIG. 9 shows moles $SiO_2$ dissolved from milled RHA, with reflux, no catalyst vs. time (hours) in Example 4 according to the embodiment of the present invention.

To a dry 2000 mL round-bottomed flask, equipped with reflux condenser kept under $N_2$; was added 60 g of milled RHA (containing 0.9 moles of $SiO_2$) and 1 L of water. The reaction was kept at 100° C. for 24 h, then the reflux condenser was switched to a distillation set-up; after 250 mL of water was distilled, 250 mL of $EGH_2$ was added. Thereafter water was distilled off and after every 250 mL of water distilled effect efficient silica dissolution by removal of water formed coincident with some $EGH_2$. The temperature was gradually increased as $EGH_2$ replaced water in the solution to approximately 200° C. Fresh $EGH_2$ was added regularly to compensate for the amount of ethylene glycol distilled off. After 16/24/30 h, 5 mL aliquots were taken, filtered, weighed and LOI was run to determine the amount of silica dissolved in the solution. The results are shown in FIGS. 8 and 9.

Example 5

Dissolution of Un-Milled RHA in $EGH_2$, No Water Reflux, with KOH Catalyst

Figure 10:
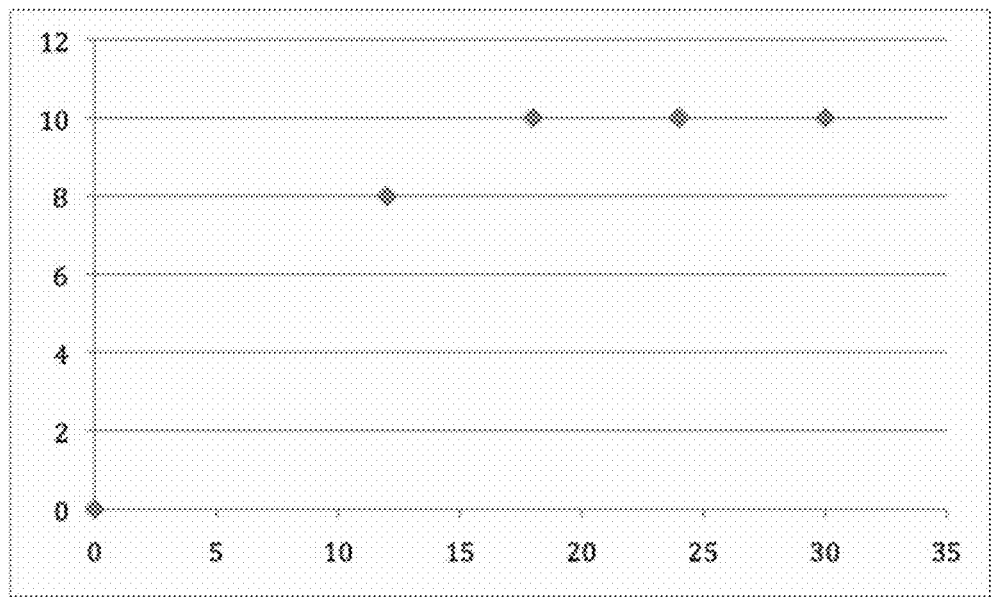
FIG. 10 shows percent silica dissolved from un-milled RHA, without reflux, with KOH catalyst, as a function of time (hours) in Example 5 according to the embodiment of the present invention, note asymptote.
Figure 11:
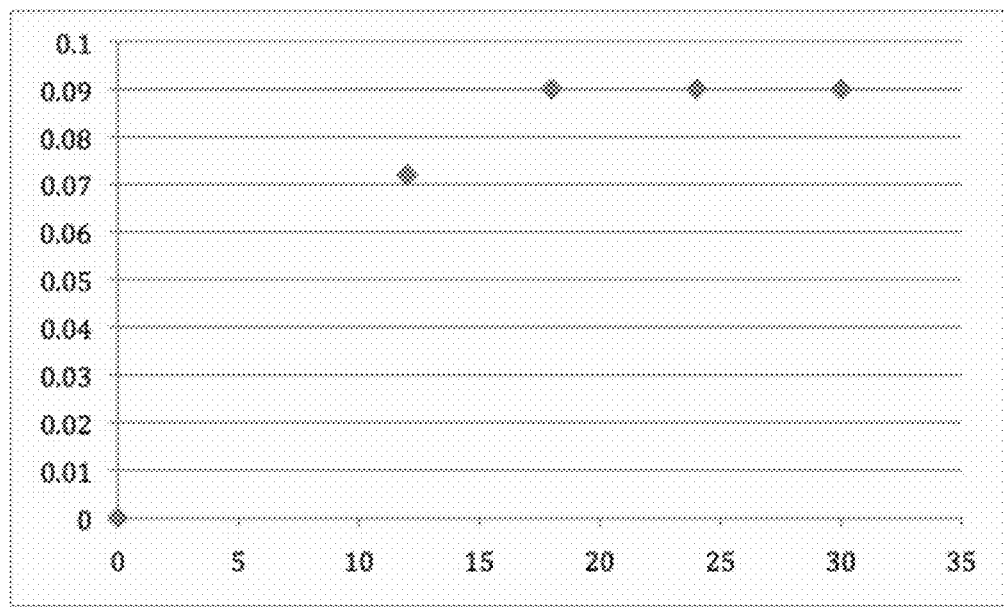
FIG. 11 shows moles $SiO_2$ dissolved from un-milled RHA, without reflux, with KOH catalyst, as a function of time (hours) in Example 5 according to the embodiment of the present invention.

To a dry 2000 mL round-bottomed flask, equipped with a distillation condenser fitted with a collection flask and kept under $N_2$; was added 60 g of untreated (as received) RHA (containing 0.9 moles of silica), 1.5 g of KOH (0.027 moles) and 1 L of $EGH_2$. The reaction was stirred magnetically and heated at 197° C. to distill out water forming with the dissolution of silica over a 30 h period. During this time, fresh $EGH_2$ was added regularly to compensate for $EGH_2$ distilled off. After 12/18/24/30 h, 5 mL aliquots were taken, filtered, weighed and then heated to conduct a loss on ignition (LOI) test, to determine the amount of silica dissolved in solution. The results are shown in FIGS. 10 and 11.

Example 6

Dissolution of Milled RHA in $EGH_2$, No Water Reflux, with KOH Catalyst

Figure 12:
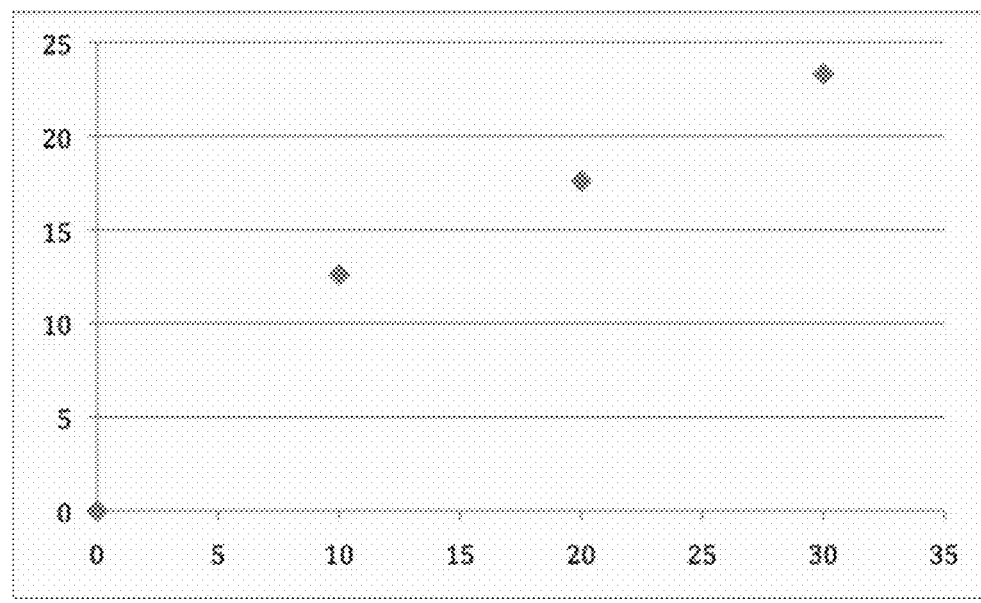
FIG. 12 shows weight percent $SiO_2$ dissolved from milled RHA, without reflux, with KOH catalyst, as a function of time (hours) in Example 6 according to the embodiment of the present invention.
Figure 13:
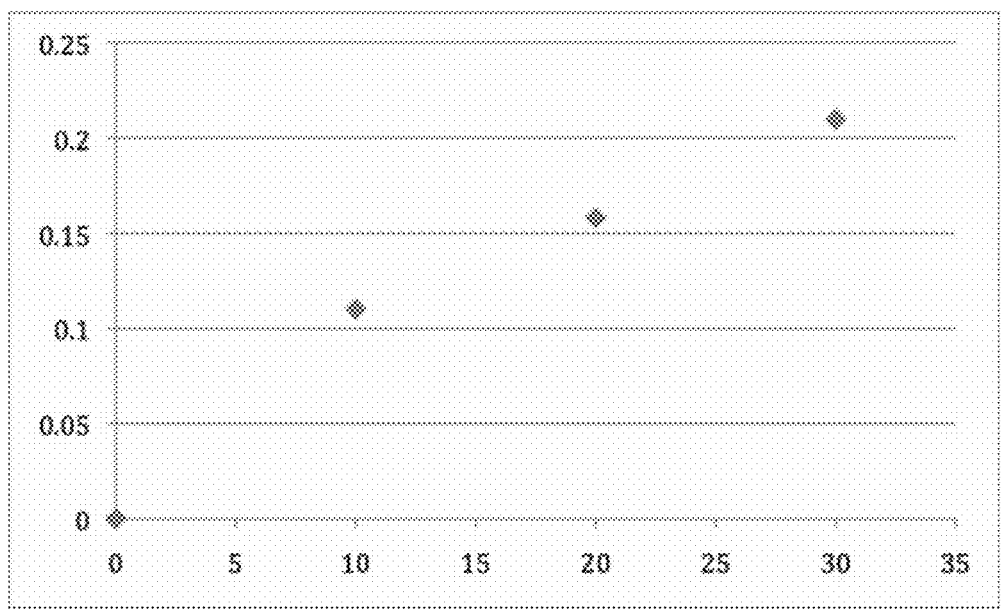
FIG. 13 shows moles of silica dissolved from milled RHA, without reflux, with KOH catalyst, as a function of time (hours) in Example 6 according to the embodiment of the present invention.

To a dry 2000 mL round-bottomed flask, equipped with a distillation condenser fitted with a collection flask and kept under $N_2$ was added 60 g of untreated RHA (containing 0.9 moles of silica), 1.5 g of KOH (0.027 moles) and 1 L of $EGH_2$. The reaction was stirred magnetically and heated at 197° C. to distill out water forming with the dissolution of silica over a 30 h period. During this time, fresh $EGH_2$ was added regularly to compensate for the amount of $EGH_2$ distilled off. After 10/20/30 h, a 5 mL aliquot was taken, filtered, weighed and then heated to conduct a loss on ignition test (LOI), to determine the amount of silica dissolved in solution. The results are shown in FIGS. 12 and 13.

Figure 14:
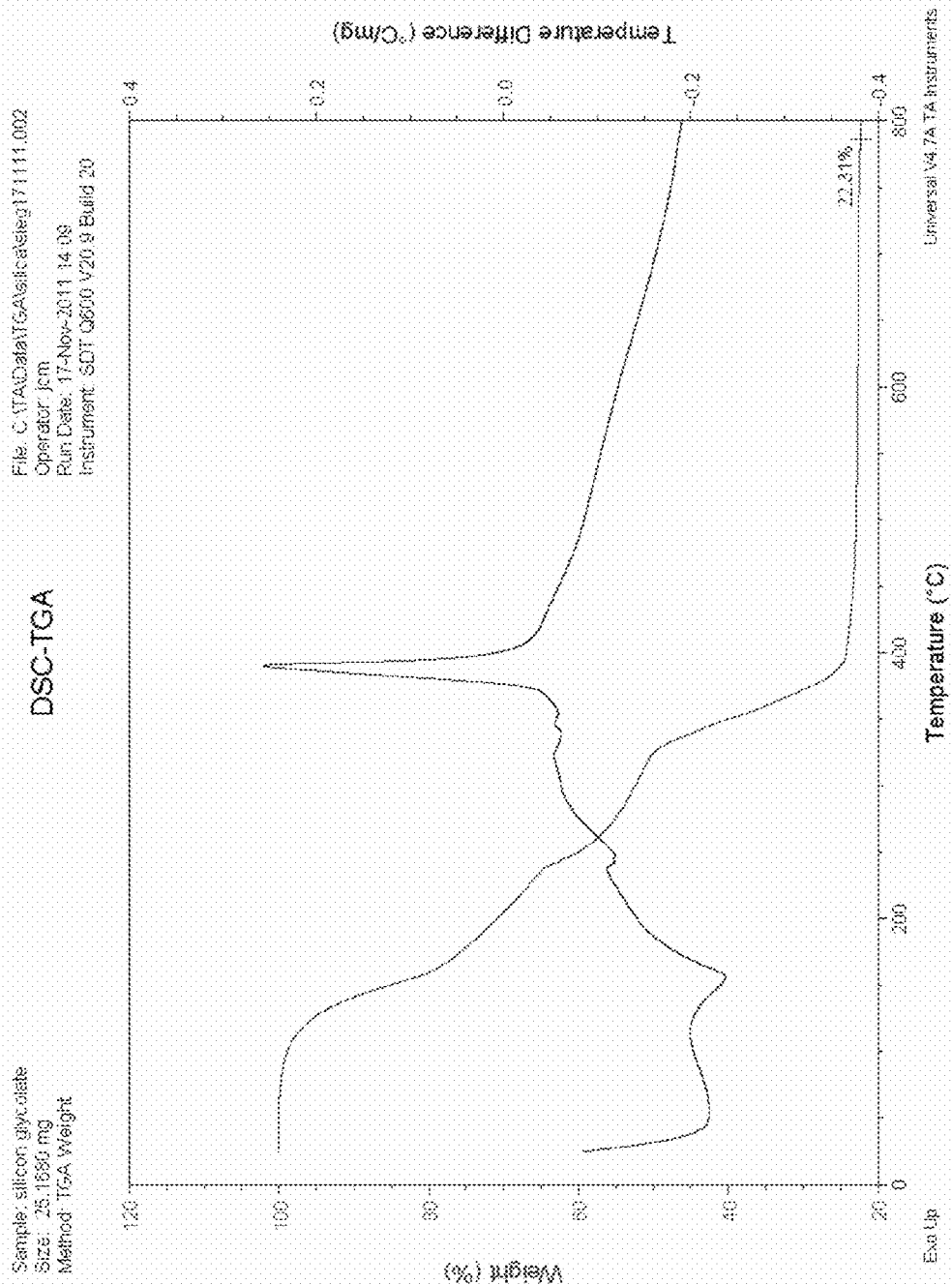
FIG. 14 shows TGA-DTA of silicon glycolate in air.

Thereafter, the silica depleted RHA was filtered off to give a solution of silicon glycolate; Si $(OCH_2CH_2OH)_4$ or $Si(EGH)_4$. This solution was concentrated by distilling off excess $EGH_2$. A typical thermogravimetric analysis such as shown in FIG. 14 indicates a ceramic yield typically of 22-24 wt %. The theoretical yield for $Si(EGH)_4$ is 22 wt %. In some instances a small amount of dimer is produced. It is possible to further distill off $EGH_2$ to produce still more dimer and higher oligomers if higher silica contents are desirable. These products are water soluble.

Example 7

Dissolution of Un-Milled RHA in $EGH_2$, with Water Reflux, with KOH Catalyst

Figure 15:
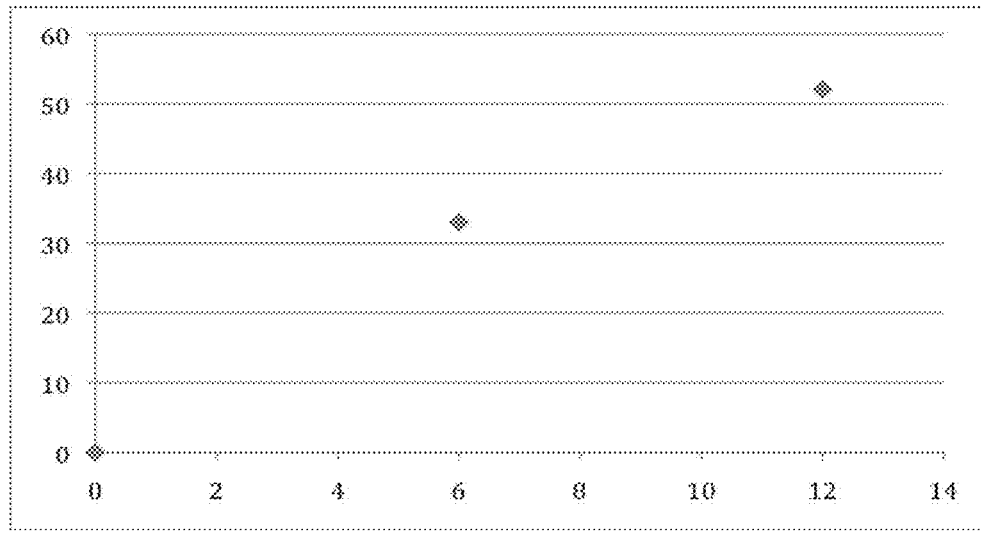
FIG. 15 shows weight percent silica dissolved from un-milled RHA, with reflux, with KOH catalyst, as a function of time (hours) in Example 7 according to the embodiment of the present invention.
Figure 16:
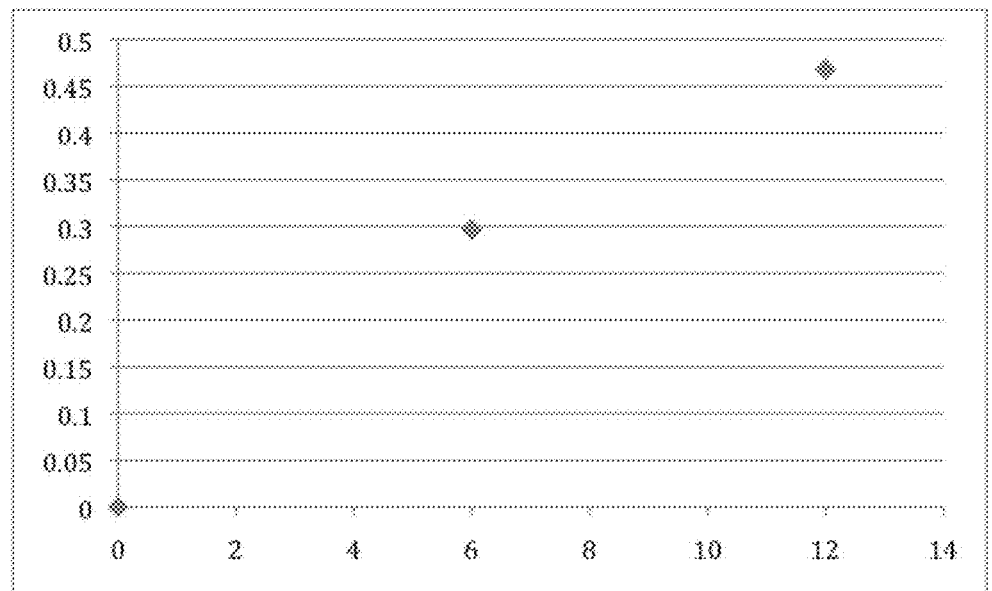
FIG. 16 shows moles of silica dissolved from un-milled RHA, with reflux, with KOH catalyst, as a function of time (hours) in Example 7 according to the embodiment of the present invention.

To a dry 1000 mL round-bottomed flask was added 60 g of unmilled RHA (containing 0.9 moles of silica), and 500 mL of water. The reaction was stirred at 100° C. for 24 h. Water was then distilled off and after every 100 mL of water distilled off; 100 mL of $EGH_2$ was added. At this point 5.0 g of KOH (0.09 moles, 10 mol %) was added and the temperature increased to ≈200° C. to effect silica dissolution by removal of water formed. Fresh $EGH_2$ was added regularly to compensate for $EGH_2$ distilled off coincidentally. After 6/12 h, 5 mL aliquots were taken, filtered, weighed and an LOI was run to determine the amount of dissolved silica. The results are shown in FIGS. 15 and 16. As can be seen, after 12 h, the total dissolution is 52 wt % above that expected if dissolution were to asymptote.

Example 8

Dissolution of Un-Milled RHA in $EGH_2$, with Water Reflux, with NaOH Catalyst

Figure 17:
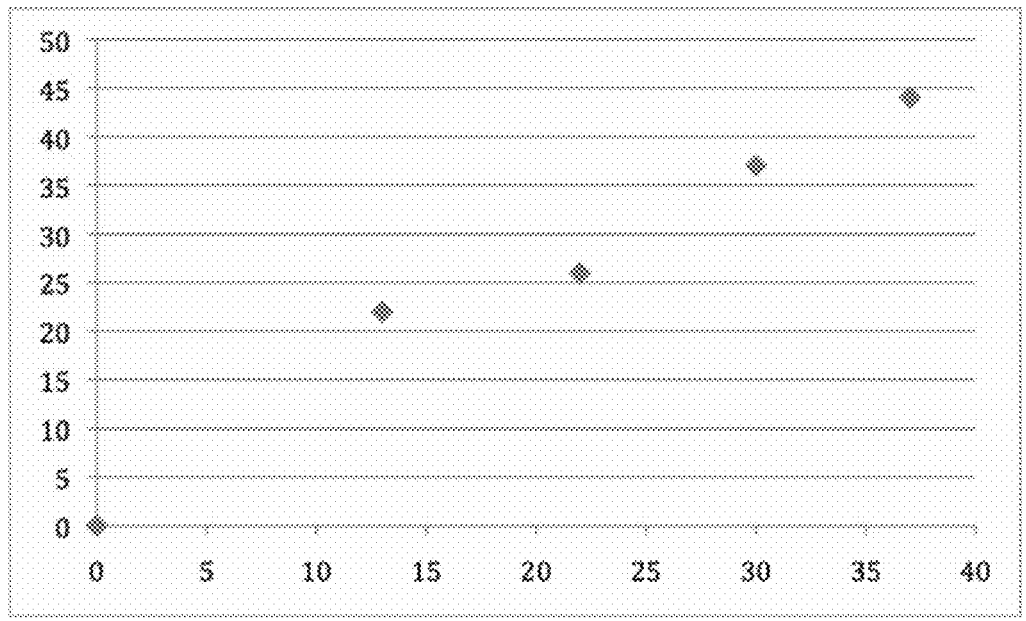
FIG. 17 shows percent silica dissolved from un-milled RHA, with water reflux, with NaOH catalyst, as a function of time (hours) in Example 8 according to the embodiment of the present invention.
Figure 18:
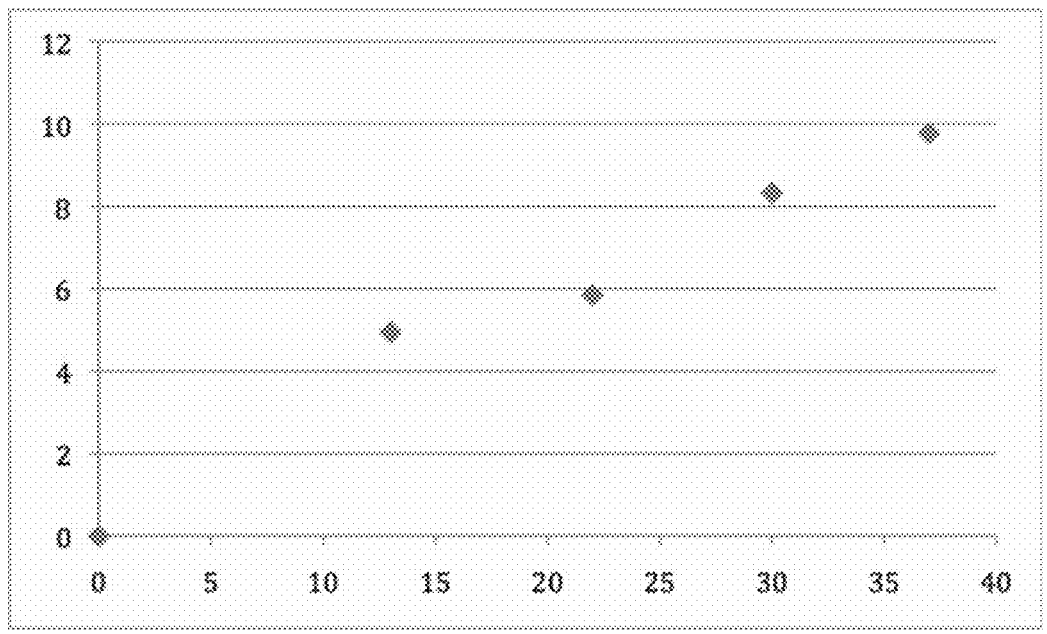
FIG. 18 shows moles of silica dissolved from un-milled RHA, with water reflux, with NaOH catalyst, as a function of time (hours) in Example 8 according to the embodiment of the present invention.
Figure 19:
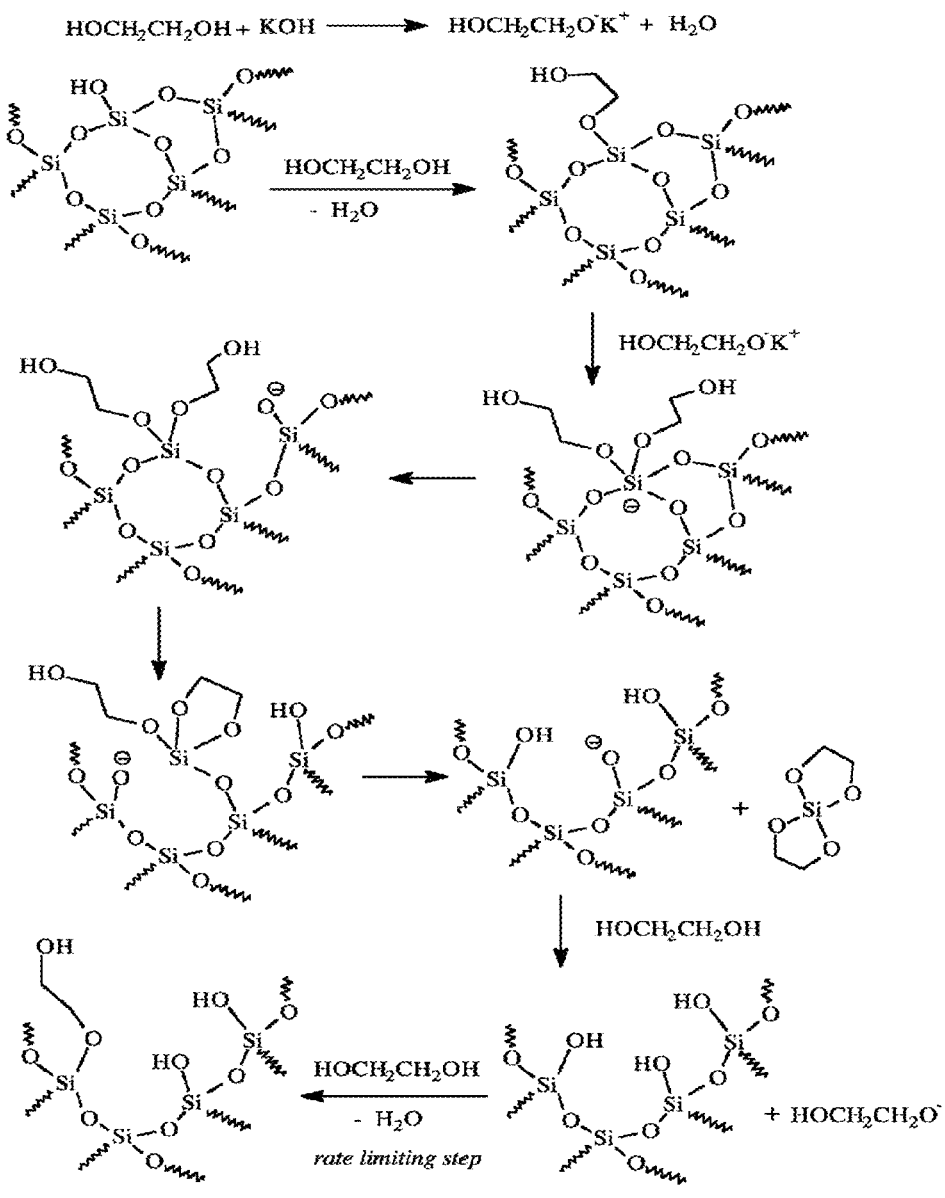
FIG. 19 shows a process Reaction (4), described in Non-Patent reference 11.
Figure 20:
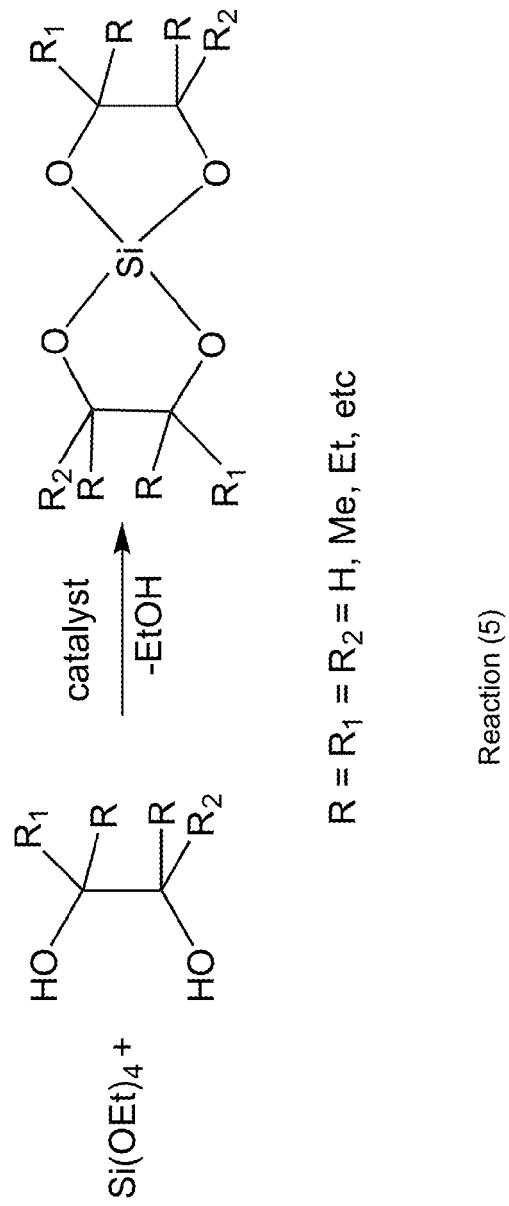
FIG. 20 shows Reaction (5) of spirosiloxanes disclosed in Non-Patent reference No. 13.

To a dry 20 L round-bottomed flask, equipped with a reflux condenser under $N_2$; was added 2.5 kg of un-milled RHA (containing 22.5 moles of silica), and 14 L of water. The reaction was stirred at 100° C. for 48 h until the pH increased to 9 or greater. Water was distilled off and after every 2 L of water distilled; 2 L of $EGH_2$ was added. At this point 160 g of KOH (4 moles) was added and the temperature increased to 197° C. Fresh $EGH_2$ was added to compensate for $EGH_2$ distilled off with the water produced by the reaction. After 13/22/30/38 h, a 5 mL aliquot was taken, filtered, weighted and then subjected to an LOI, to determine the amount of silica dissolved in the solution. The results are shown in FIGS. 17 and 18.

Example 9

Dissolution of Acid Milled Bagasse

Received bagasse was sieved, charred at 600° C., milled in dilute acid and neutralized. To a dry 1000 ml round-bottom flask equipped with a reflux condenser and kept under $N_2$ was added 60 g of treated bagasse (containing 0.99 moles of $SiO_2$), 168 ml of water, and 168 ml of $EGH_2$. The reaction was stirred at reflux for 24 h and then the water was distilled out and replaced with $EGH_2$. At this point, 1.6 g of NaOH (0.04 moles) was added, the temperature increased to 197° C., and distillation continued. Fresh $EGH_2$ was added to compensate for $EGH_2$ distilled out with the water produced by the reaction. After 5/10/20/30/40 h, a 5 ml aliquot was taken, filtered, weighted and then subjected to an LOI to determine the amount of silica dissolved in the solution. After 40 h, the total dissolution was 27% dissolved silica. The solution was filtered through a filter paper and a glycoxy silane (GS) solution was collected (~100 ml with ceramic yield ~5 wt.%).

Example 10

Dissolution of Diatomaceous Earth

To a dry 22 L round-bottom flask equipped with a reflux condenser and kept under $N_2$ was added 2.5 kg of diatomaceous earth (containing 35.4 moles of $SiO_2$), 7 L of water, and 7 L of $EGH_2$. The reaction was stirred at reflux for 24 h and then the water was distilled out and replaced with $EGH_2$. At this point, 59 g of NaOH (1.475 moles) was added, the temperature increased to 197° C., and distillation continued. Fresh $EGH_2$ was added to compensate for $EGH_2$ distilled out with the water produced by the reaction. After 14/20/30 h, a 5 ml aliquot was taken, filtered, weighted and then subjected to an LOI to determine the amount of silica dissolved in the solution. After 30 h, the total dissolution was 33% dissolved silica. The solution was filtered through a filter paper and a glycoxy silane (GS) solution was collected (~8 L with ceramic yield ~5 wt.%).

Example 11

Dissolution of Acid-Milled RHA in 1,2 Propanediol, No Water Reflux, with NaOH Catalyst and Toluene To a dry 1000 mL round-bottomed flask, equipped with a distillation condenser fitted with a collection flask and kept under $N_2$; was added 25 g of acid-milled, neutralized and dried RHA (containing 0.38 moles of silica), 1.5 g of NaOH (0.037 mol) dissolved in 10 mL water, and 300 mL of 1,2 Propanediol (b.p. 187° C.). Then 150 mL of toluene was added and the reaction was stirred magnetically and heated to approximately 100-110° C. to distill out the water and toluene over a 13 h period. All the toluene was distilled out and a loss on ignition test (LOI) was performed, to determine the amount of silica dissolved in solution. It was calculated that 23% silica dissolved (0.08 moles of silica, adjusted: 0.06 mol by substracting moles of sodium alcoholate that formed). Then, the 1,2 Propanediol was continued distilling over 15-h-period. Another LOI was performed at ~29 h distillation time and calculated ~31% dissolved silica (0.10 mol, adjusted: 0.08 mol by subtracting moles of sodium alcoholate that formed).

Example 12

Dissolution of Acid-Milled RHA in 1,4 Butanediol, No Water Reflux, with NaOH Catalyst and Toluene To a dry 1000 mL round-bottomed flask, equipped with a distillation condenser fitted with a collection flask and kept under $N_2$; was added 25 g of acid-milled, neutralized and dried RHA (containing 0.38 moles of silica), 1.5 g of NaOH (0.037 mol) dissolved in 10 mL water, 400 mL of 1,4 Butanediol (b.p. 230° C.). Then 150 mL of toluene was added and the reaction was stirred magnetically and heated to approximately 100-110° C. to distill out the water and toluene over a 14 h period. All the toluene was distilled out and a loss on ignition test (LOI) was performed, to determine the amount of silica dissolved in solution. It was calculated that 4.7% silica dissolved. Then, the 1, 4 Butanenediol was continued distilling over 20 -h-period (total ~36 h), and another LOI was performed at ~36 h. It was calculated ~32% dissolved silica (0.12 mol, adjusted: 0.093 mol after subtraction for sodium alcoholate formed).

Example 13

Sodium Glycolato Silicate (SGS) Used as a Catalyst

To a 1000 ml round bottom flask, equipped with a distillation condenser and magnetic stirring and kept under $N_2$ were placed 60 g (0.9 moles of silica) of RHA (twice acid milled, neutralized with ammonium hydroxide, dried at 70° C. for a week) with 500 mL of ethylene glycol. The solution was heated to distill 250 mL of over 5 h to remove residual water. To this was added a solution of 0.072 moles of SGS (16.74 g or 8 mol % of the silica) dissolved in 250 mL of ethylene glycol. The initial TGA of this sample showed a ceramic weight of 1.56%. The theoretical ceramic weight from the SGS in that solution is 1.54%. In total there is 58.3 g of $SiO_2$ in the system (4.3 g of it coming from the dissolved SGS and therefore not in the form of $SiO_2$) and the equivalent of 2.23 g of $Na_2O$ equivalents. Fresh $EGH_2$ was added regularly to keep the reaction volume constant. Samples were taken at 5/11/17/23 hours, filtered then analyzed by TGA-DTA with the results shown in Table 1.

Example 14

Silica Precipitation Using Formic Acid Addition (Glycoxy Silane Solution Obtained from NaOH Catalyzed RHA Extraction)

Distilled water (150 mL) was introduced to a 1-L-reactor, equipped with a magnetic stirrer. Glycoxy silane solution (50 g, CY ~18 wt. %) was added with vigorous stirring and then 16 mL of formic acid (10%) was added drop-wise to adjust the pH to 6. After the acid addition, the mixture was left stirring vigorously at RT for 30 min. Then mixture was filtered. The obtained white silica was then washed in hot water and hot methanol and filtered. The silica powder was oven dried at 70° C. The yield minus mechanical losses is ≈85% with typical specific surface areas (SSA=500-600 $m^2/g$): SSA=582 $m^2/g$, PSD (0.79 cm3/g), Pore size ~4-5 nm.

Example 15

Silica Precipitation Using Hot Water Precipitation (Glycoxysilane Obtained from KOH Catalyzed RHA Extraction)

To a dry 12-L-reactor, equipped with a mechanical stirrer and a heating mantle, was added 1440 g of concentrated glycoxy silane solution, CY ≈15 wt.% with vigorous stirring to 2.5 L of water pre-heated to 80° C. The solution was stirred for 1 h, cooled down and filtered. The obtained silica was then stirred in 2 L of hot HCl (10%) for 2 h and filtered and washed with hot water and methanol giving an ~80% yield of white powder after drying at 70° C. overnight. The SSA was found to be 470 $m^2/g$.

What is claimed is:

1. A method of producing alkoxysilane and precipitated silica from biogenic silica; wherein biogenic silica is rice hulls, comprising the steps of:
    a first step of mixing the biogenic silica with a polyol to obtain a mixture so that the mixture is heated to distill water;
    a second step of adding a base to the mixture to obtain a reaction mixture;
    a third step of filtering the reaction mixture to obtain alkoxysilane; and
    a fourth step of purifying alkoxysilane to obtain the precipitated silica.

2. The method according to claim 1, wherein, in the first step, said polyol includes at least one of ethylene glycol, 1,2-diol 1,3-diol, 2,3-diol, 1,4-diol, glycerol, triethanolamine, trishydroxy-methylamine, and a mixture thereof.

3. The method according to claim 1, wherein, in the second step, said base includes at least one of LiOH, NaOH, KOH, CsOH, RbOH, and a mixture thereof.

4. The method according to claim 1, wherein, in the second step, said base is added in an amount of 0.25-50 mol % in a form of a solid or a solution thereof dissolved in a solvent.

5. The method according to claim 1, further comprising the step of neutralizing alkoxysilane to eliminate an alkali metal base.

6. The method according to claim 1, further comprising the step of purifying the reaction mixture by distillation or extraction with a solvent that does not or only minimally dissolves the diol.

7. The method according to claim 1, wherein, in the second step, said reaction mixture is maintained at a temperature of 140-250° C. under atmospheric pressure.

8. The method according to claim 1, wherein, in the second step, a liquid including benzene or toluene is added to the reaction mixture to form azeotrope water so that a temperature is reduced from a boiling point of the diol.

9. The method according to claim 1, wherein, in the second step, said reaction mixture is maintained at a temperature of 140-250° C. under pressure of 2-200 atmospheres.

10. The method according to claim 1, wherein said second step is stopped after a silica content thereof reaches greater than about 20 wt % of that originally present in the biogenic silica so that the reaction mixture is filtered to obtain a solution with a silica content of 15-40 wt % containing both alkoxysilane and a silicon alcoholate so that the silicon alcoholate precipitates and can be filtered off on cooling.

\* \* \* \* \*